United States Patent
Krokoszinski et al.

(10) Patent No.: US 9,006,495 B2
(45) Date of Patent: Apr. 14, 2015

(54) PROCESS FOR THE CATALYTIC ALDOL CONDENSATION OF ALDEHYDES

(71) Applicant: BASF SE, Ludwigshafen (DE)

(72) Inventors: Roland Krokoszinski, Weisenheim am Berg (DE); Steffen Oehlenschläger, Bad Dürkheim (DE); Rainer Papp, Speyer (DE); Jens Rudolph, Worms (DE); Armin Ulonska, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/091,991

(22) Filed: Nov. 27, 2013

(65) Prior Publication Data

US 2014/0155656 A1 Jun. 5, 2014

Related U.S. Application Data

(60) Provisional application No. 61/731,493, filed on Nov. 30, 2012.

(51) Int. Cl.
*C07C 45/72* (2006.01)
*C07C 45/74* (2006.01)

(52) U.S. Cl.
CPC .................... *C07C 45/74* (2013.01)

(58) Field of Classification Search
USPC .......................................... 568/464; 422/187
See application file for complete search history.

(56) References Cited

U.S. PATENT DOCUMENTS

| | | |
|---|---|---|
| 2,848,498 A | 8/1958 | Mention |
| 5,434,313 A | 7/1995 | Harrison et al. |
| 6,340,778 B1 | 1/2002 | Bueschken et al. |
| 2012/0123169 A1 | 5/2012 | Kaizik et al. |
| 2013/0131416 A1 | 5/2013 | Crone et al. |
| 2013/0237726 A1 | 9/2013 | Krokoszinski et al. |
| 2013/0274525 A1 | 10/2013 | Zeller et al. |

FOREIGN PATENT DOCUMENTS

| | | |
|---|---|---|
| DE | 927 626 C | 5/1955 |
| EP | 1 106 596 A2 | 6/2001 |
| GB | 734000 A | 7/1955 |
| WO | WO-93/20034 A1 | 10/1993 |
| WO | WO-2010/105892 A1 | 9/2010 |
| WO | WO-2012/145241 A1 | 10/2012 |

OTHER PUBLICATIONS

Tebel, K. H., et al., "Der Freistrahlrohrreaktor—Ein Effektives Reaktor-Design zur Unterdrückung von Selektrivitätsverlusten durch Schnele, Unerwünschte Folgereaktionen", Chem.-Ing.-Tech., 1988, vol. 60, No. 11, pp. 912-913.
U.S. Appl. No. 61/476,593.
U.S. Appl. No. 14/053,634, Tschirschwitz et al.
International Search Report for PCT/EP2013/075029 dated Apr. 29, 2014.

*Primary Examiner* — Sikarl Witherspoon
(74) *Attorney, Agent, or Firm* — Drinker Biddle & Reath LLP

(57) ABSTRACT

The present invention relates to a process for the catalytic aldol condensation of aldehydes, in particular for preparing α,β-unsaturated aldehydes, in a multiphase reactor.

17 Claims, 2 Drawing Sheets

PROCESS FOR THE CATALYTIC ALDOL CONDENSATION OF ALDEHYDES

CROSS-REFERENCE TO RELATED APPLICATIONS

This application claims benefit (under 35 USC 119(e)) of U.S. Provisional Application No. 61/731,493, filed Nov. 30, 2012, which is incorporated by reference.

BACKGROUND OF THE INVENTION

The present invention relates to a process for the catalytic aldol condensation of aldehydes, in particular for preparing α,β-unsaturated aldehydes, in a multiphase reactor.

PRIOR ART

Unsaturated aldehydes are starting materials for the preparation of many organic compounds and are used in many applications. They can, inter alia, be hydrogenated to produce saturated alcohols which in turn serve as starting materials for the production of plasticizers, detergents or solvents. In addition, the unsaturated aldehydes can be converted by selective hydrogenation into the saturated aldehydes and by subsequent oxidation into carboxylic acids.

Unsaturated aldehydes are prepared industrially by aldol condensation of saturated aldehydes with elimination of water. Important aldol condensations are the reaction of n-butyraldehyde with elimination of water to form 2-ethylhexenal or the reaction of n-valeraldehyde with elimination of water to form 2-propylheptenal. The starting materials can comprise not only the linear aldehydes but also branched aldehydes which can undergo an aldol condensation with themselves, with other branched aldehydes or with linear aldehydes, Likewise, aldehydes having different numbers of carbon atoms can be condensed with one another in an aldol reaction. The two hydrogenation products of the aldehydes 2-ethylhexenal and 2-propylheptenal (or isomer mixtures thereof) obtained by aldol condensation are 2-ethylhexanol and 2-propylheptanol (or isomer mixtures thereof) and are used on a large scale, inter alia as plasticizer alcohols.

As catalyst for the aldol condensation, use is generally made of a base, often NaOH, dissolved in water, with the aqueous base forming a second liquid phase in addition to the organic starting material/product mixture. The water of reaction liberated during the reaction becomes concentrated in the heavier, aqueous phase. The organic starting materials and products form the lighter, organic phase. The reaction temperature of the aldol condensation is typically in the range from 80 to 180° C. The reaction is generally carried out under a superatmospheric pressure which, in the presence of a gas phase, corresponds to the sum of the vapor pressures of aqueous and organic phases and is typically below 10 bar. Heat is liberated during the reaction and has to be removed from the process. The aldol condensation typically proceeds with high selectivity (>95%) to the desired products. An important secondary reaction is the formation of high-boiling by-products. A further possible secondary reaction is the Cannizzaro reaction which also leads to consumption of the catalyst.

Since the catalyst used in the aldol condensation is present essentially in the aqueous phase, the reaction likewise takes place mainly in the aqueous phase. To achieve a sufficiently rapid reaction, the starting materials therefore have to be similarly readily soluble in the aqueous phase. This is no longer the case for aldehydes having more than 6 carbon atoms, so that economical operation without solvent and/or solubilizer is often no longer possible here.

The reaction volume available for the aldol condensation is set by the volume of the aqueous phase. It is therefore desirable to operate the reactor with the highest possible proportion of aqueous phase. In the case of a continuous reaction, the aqueous phase leaving the reactor is usually, after phase separation, recirculated to the reactor for this reason. Such a mode of operation is described, for example, in EP 1106596 A2. Owing to the dilution of the aqueous phase by the water of reaction formed, part of the aqueous phase has to be continually discharged from the process and catalyst has to be replaced.

To ensure sufficiently good mass transfer between the two liquid phases, an appropriately large phase interface should also be made available in the reactor. This is typically achieved by introducing mixing energy by means of a dispersing apparatus. However, this mixing energy should not be too great since otherwise a stable emulsion of the two phases can be formed; this emulsion then cannot be separated completely by simple methods, e.g. in a simple gravity separator, after the reaction mixture leaves the reactor.

Various types of reactor have been used in the past for carrying out the aldol condensation of aldehydes. The aldol condensation can, for example, be carried out in a stirred reactor in which the two liquid phases are dispersed. Such processes are described, for example, in DE 927626 and WO 1993/20034. A disadvantage of this process is the use of mechanically susceptible rotating parts. Furthermore, removal of the heat of reaction via structurally complicated internal heat exchanger tubes is necessary.

U.S. Pat. No. 5,434,313 describes the use of three mixing circuits in series for the aldol condensation of n-butyraldehyde. The mixing energy is provided by the three pumps of the mixing circuit. To increase the residence time, a vessel is integrated into each of the second and third circuits. Disadvantages of this reaction system are the large outlay for installation of the tubes and the large number of circulation pumps required.

Furthermore, U.S. Pat. No. 5,434,313 describes carrying out the aldol condensation in a tube reactor. To achieve better dispersion of the two liquid phases, static mixing elements or packing are/is provided. The removal of heat is said to occur via the tube wall. Disadvantages of this concept are the large tube length required and the complicated way in which heat is removed.

EP 1106596 A2 likewise proposes the use of a tube reactor which is equipped with mixing elements. The discharge from the tube reactor is fed to a phase separator for separation of the two liquid phases. Part of the aqueous phase is recirculated together with the catalyst dissolved therein to the reactor, and the remainder is discharged from the process. As a result of this mode of operation, an excess of aqueous phase is established in the reactor, and the organic phase is present as a dispersion in the aqueous phase. The heat of reaction is removed from the recirculated aqueous phase by means of an external heat exchanger. To achieve sufficient dispersion of the organic phase, a high flow velocity in the tube reactor used is necessary; this leads to a relatively high pressure drop. An advantage of this reactor concept is the backmixing-free reaction of the organic starting materials. However, this is associated with a number of disadvantages such as the large tube length required and the associated large number of mixing elements. In addition, a high energy input is necessary for dispersing the organic phase and this requires the use of larger pumps and thus a higher power consumption. The typical pressure drop for the packing elements indicated, e.g. SMV2 from Sulzer and VFF, is 150 mbar/m. A typical power input of from 50 to 80 kW/m³ of liquid volume can be calculated therefrom for the process described in EP 1106596 A2.

It is an object of the invention to provide an improved process for the catalytic aldol condensation in a two-phase liquid reaction mixture. This should be suitable for the aldol condensation of aldehydes with high selectivity to form the unsaturated aldol condensation product (unsaturated aldehyde). In particular, it is an object of the invention to provide a process for the catalytic aldol condensation
  which has a compact reactor construction,
  in which a large proportion of aqueous phase can be set in the reactor in a simple way without aqueous phase having to be recirculated to the reactor from an external separator,
  in which the removal of heat is carried out in a simple manner,
  and in which satisfactory dispersion of the organic phase can be achieved with a very low energy input.

It has surprisingly been found that the stated object can be achieved effectively when both the reaction and the coalescence of the two liquid phases are combined in one apparatus. For this purpose, the settling out of the heavier aqueous phase is made possible by means of an unmixed disengagement zone through which flow occurs slowly in an upward direction in the upper part of the apparatus. As a result, this aqueous phase becomes concentrated in the mixed reaction zone underneath.

SUMMARY OF THE INVENTION

The invention provides a process for the catalytic aldol condensation of at least one aldehyde in a two-phase liquid reaction mixture in a reactor which has a reaction zone and a disengagement zone located directly above the reaction zone, wherein an aldehyde-comprising phase dispersed in a continuous aqueous catalyst-comprising phase is produced and a stream of the two-phase reaction mixture is allowed to rise from the reaction zone into the disengagement zone and coalesce, with a continuous organic phase being formed in the upper region of the disengagement zone.

The invention further provides for the use of an apparatus comprising a reactor which has reaction zone and a disengagement zone located directly above the reaction zone, wherein the reaction zone has a device for producing an organic phase dispersed in a continuous aqueous phase and the disengagement zone allows the coalescence of the two-phase reaction mixture and the formation of a continuous organic phase in the upper region of the disengagement zone, for reaction of a two-phase liquid reaction mixture.

DESCRIPTION OF THE INVENTION

For the purposes of the invention, the term "aqueous phase" refers to the phase which comprises water as main component. If the organic compounds comprised in the reaction mixture have some miscibility with water, the aqueous phase can accordingly comprise proportions of dissolved organic compounds. Correspondingly, the term "organic phase" refers, for the purposes of the invention, to the phase which comprises organic compounds, e.g. the aldehydes used for the aldol condensation and the products of the aldol condensation, as main component.

The process of the invention makes it possible for reaction zone and disengagement zone to be located in a single reaction vessel.

The process of the invention is preferably carried out continuously.

The aqueous catalyst-comprising phase comprises largely water. If desired, the aqueous phase can additionally comprise at least one organic, water-miscible solvent. Organic solvents which can be used are, for example, propanediol, glycerol, diethylene glycol and dimethylformamide.

The proportion of water and organic solvent in the aqueous phase is preferably at least 60% by weight, particularly preferably at least 80% by weight, based on the total weight of the aqueous phase.

In a preferred embodiment, the aqueous phase does not comprise any added organic solvents. For the purposes of the invention, the amount of aldehyde starting material, products of the aldol condensation and reaction-typical impurities dissolved in the aqueous phase do not count as added organic solvents. The proportion of water in the aqueous phase is then preferably at least 60% by weight, particularly preferably at least 80% by weight, based on the total weight of the aqueous phase.

The aqueous phase can optionally comprise phase transfer agents, surface-active or amphiphilic reagents or surfactants.

Preferred catalysts for the process of the invention are water-soluble, basic compounds such as hydroxides, hydrogencarbonates, carbonates, carboxylates or mixtures thereof in the form of their alkali metal or alkaline earth metal compounds. Preference is given to using alkali metal hydroxides, such as sodium hydroxide.

The concentration of the catalyst in the continuous aqueous phase in the reaction zone is preferably in the range from 0.1 to 15% by weight, particularly preferably from 0.2 to 5% by weight, in particular from 1 to 3% by weight.

The process of the invention is suitable for the reaction of aldehydes or aldehyde mixtures which can undergo a condensation reaction. If only one aldehyde is used, this has to have two α-hydrogen atoms on the same carbon atom next to the CO group. If two or more different aldehydes are used, at least one of the aldehydes has to have two α-hydrogen atoms on the same carbon atom.

Suitable aldehydes for the process of the invention are aldehydes having from 1 to 15, preferably from 3 to 15, particularly preferably from 4 to 6, carbon atoms.

Suitable aldehydes having two α-hydrogen atoms are, for example, acetaldehyde, propanal, n-butyraldehyde, n-valeraldehyde, 3-methylbutyraldehyde, n-hexanal, 3-methylpentanal, 4-methylpentanal, n-heptanal, n-octanal, n-nonanal and n-decanal. These aldehydes are also suitable for a homo-condensation.

Suitable aldehydes having one α-hydrogen atom are, for example, isobutyraldehyde, 2-methylbutyraldehyde, 2-methylpentanal, 2-ethylhexanal, cyclohexylaldehyde.

Preferred starting materials for the process of the invention are: n-butyraldehyde, n-valeraldehyde, mixtures of n-butyraldehyde and isobutyraldehyde, mixtures of n-valeraldehyde with 2-methylbutyraldehyde and/or 3-methylbutyraldehyde. It is likewise possible to use a mixture of $C_4$- and $C_5$-aldehydes. These aldehydes can be prepared, for example, by hydroformylation of olefins.

When more than one aldehyde or an aldehyde mixture are/is used, the individual components can be fed separately into the stream of the catalyst solution. It is likewise possible to mix all starting materials before they are fed in and to feed them in together. Furthermore, the aldehydes can be used as a solution. Solvents which can be used are inert liquids which are sparingly soluble in the catalyst solution, for example hydrocarbons such as pentane, hexane, ligroin, cyclohexane or toluene.

Reaction Zone

According to the invention, the aqueous phase forms the continuous phase of the two-phase reaction mixture in the reaction zone. The proportion by volume of the aqueous phase in the reaction zone is preferably at least 70%, particularly preferably at least 80%, based on the total volume of the two-phase reaction mixture in the reaction zone.

In the process of the invention, the proportion of aqueous phase in the reaction zone is thus generally substantially greater than in a mixed reactor of the prior art without disengagement zone at the same reaction conversion. In the latter, an organic continuous phase would be established in the reaction zone without an externally introduced aqueous stream; such an organic continuous phase would have adverse consequences for the conversion and selectivity of the reaction.

The proportion by volume of the aqueous phase in the reaction zone can be set by, inter alia, appropriate design of the disengagement zone (e.g. the volume, type and extent of any internals and/or packing) so that the aqueous phase represents the continuous phase in the reaction zone.

The reaction zone is preferably backmixed. In particular, use is made of a reaction zone which is fluid-dynamically backmixed in respect of the aqueous phase and in respect of the organic phase (i.e. virtually equal concentrations of the aqueous phase and the organic phase are present at all points in the reaction zone). Mixing serves for macroscopic mixing of the reaction zone and for dispersing the organic phase as small droplets in the continuous aqueous phase. It has been found that backmixing in the reaction zone has a positive effect on the selectivity of the process. As a result of backmixing, the steady-state concentration of starting material is low and high-boiling condensation products are therefore formed to a lesser extent. Likewise, the removal of the heat of reaction from a circulated backmixed system is simpler since, for example, it is possible to employ an external heat exchanger.

In a specific embodiment of the process of the invention, at least one stream fed into the reaction zone and/or at least one stream from the reaction zone conveyed in an external circuit (circulation stream) is/are used for backmixing.

Suitable mixing devices are, for example, dynamic mixers (i.e. mixers whose mixing elements comprise movable parts) and static mixers (i.e. mixers without moving parts in the interior, which, in particular, operate according to the in-line principle). Preference is given to using at least one mixing device selected from among mixing nozzles, stirrers, mixing pumps, static mixing elements, beds of random packing elements, etc. Suitable types of stirrer comprise, for example, propeller stirrers, impeller stirrers, disk stirrers, blade stirrers, anchor stirrers, inclined blade stirrers, crossed-beam stirrers, helical stirrers, stirring screws, etc.

Preference is given to using at least one mixing nozzle for producing the aldehyde-comprising phase dispersed in the continuous aqueous catalyst-comprising phase in the reaction zone. Here, only a low power input is preferably effected by means of the mixing power of the nozzle. The total mixing power introduced into the reactor is preferably not more 0.5 kW per $m^3$ of liquid volume, particularly preferably not more than 0.3 kW per $m^3$ of liquid volume. This is a substantial difference from the process described in EP 1 106 596, in which, as indicated above, the mixing power is from 50 to 80 kW/$m^3$ and thus two orders of magnitude greater.

The reaction zone is preferably configured as a loop reactor or as a stirred vessel. Suitable loop reactors are, for example, free jet reactors, jet loop reactors, jet nozzle reactors, etc.

In a preferred embodiment, the reaction zone is configured as a free jet reactor. Free jet reactors and their design are described, for example, in K. H. Tebel, H.-O. May, Chem.-Ing.-Tech. 60 (1988), No. 11, pp. 912-913, and the references cited therein, which are hereby incorporated by reference.

The aldehyde is preferably introduced into the reaction zone in the region of the high local mixing energy of the mixing device, for example in the vicinity of the stirrer blades of a stirrer or at the nozzle tip of a mixing nozzle. This ensures good dispersing and mixing-in of the aldehyde in the aqueous reaction zone.

The introduction and mixing-in of the aldehyde occurs particularly advantageously when it is introduced via a two-fluid nozzle. A diagram of a suitable two-fluid nozzle may be found in Ullmann's Encyclopedia of Industrial Chemistry, 5th Edition, Volume B 4, page 280, FIG. 6, A and is referred there as "two-phase jet nozzle". The associated article describes two-phase streams composed of a gas phase and a liquid phase. However, the nozzle depicted can be used for liquid/liquid two-phase streams in the process of the invention. The aqueous phase is then preferably introduced where "liquid" is indicated in the drawing and the organic phase is fed into the annular space where "gas" is indicated in the drawing.

As an alternative, it is possible to feed the aldehyde into a stream from the reaction zone conveyed in an external circuit (circulation stream).

In addition to the aldehyde, catalyst also has to be fed into the reaction zone. The introduction of the catalyst is preferably effected into a stream from the reaction zone conveyed in an external circuit (circulation stream). The introduction of the catalyst is then preferably carried out on the suction side (upstream) of the transport device comprised in the circulation stream. If the catalyst is added on the suction side of, for example, a circulation pump, good mixing advantageously takes place in the pump. The catalyst is generally introduced in the form of a concentrated aqueous solution.

In a preferred embodiment of the process of the invention, the reaction zone is configured as a free jet reactor. Here, part of the reaction mixture is taken off from the reaction zone and returned via a nozzle in the upper region of the reaction zone. Preference is given to taking off part of the reaction mixture in the lower region of the reaction zone and especially at the bottom end. This produces circular flow in the reaction zone. A two-fluid mixing nozzle is preferably used as nozzle. The introduction of the circulation stream and the introduction of the aldehyde into the reaction zone are preferably effected via the two-fluid mixing nozzle. The nozzle is preferably directed axially downward in the reaction zone. In a preferred embodiment, an impingement plate is present at the lower end of the reaction zone.

The heat of reaction evolved in the aldol condensation can, in a useful embodiment, be removed directly in the reaction zone by means of integrated heat exchangers. In a preferred embodiment, an external heat exchanger integrated into a circuit is used for removal of heat.

The removal of heat is in this case effected inexpensively via an external heat exchanger which is integrated into the circuit leading to and from the reactor. The circulated stream preferably at the same time provides the driving jet of the nozzle and thus ensures mixing of the apparatus. The circulation pump of the external circuit draws in predominantly aqueous phase from the lower region of the reaction zone, as a result of which the risk of formation of a stable emulsion which can no longer be coagulated by simple settling is minimized.

Disengagement Zone

In the disengagement zone, a phase inversion takes place, i.e. the emulsion composed of a continuous aqueous phase and a disperse organic phase in the reaction zone is inverted to form an emulsion composed of a continuous organic phase and a disperse aqueous phase in the disengagement zone.

The cross-sectional area of the disengagement zone has to be sufficiently large for a phase separation to be able to take place and the aqueous phase to be able to settle in countercurrent. The diameter of the part of the apparatus in which the disengagement zone is located can therefore differ from the diameter of the part of the apparatus in which the reaction zone is located.

The upward-directed superficial velocity of the two liquid phases in the disengagement zone should preferably be less than 10 mm/s. It should particularly preferably be less than 5 mm/s. The velocity reported is calculated on the basis of the empty tube even when using internals and/or packing.

In a preferred embodiment, the disengagement zone comprises internals and/or packing. Packing can be used in the form of (ordered) packing or as a bed of random packing elements. This enables better coalescence of the two phases to be achieved in the disengagement zone.

Examples of internals are filter plates, baffles, column trays, perforated plates or other devices also used as mixing devices. Further suitable internals are a plurality of narrow, parallel tubes to form a multitube reactor. Particular preference is given to structured mixer packings or demister packings. Suitable packing elements are, for example, Raschig rings, saddles, Pall rings, Tellerettes, wire mesh rings or woven wire meshes. Steel has been found to be an advantageous material for packings and packing elements since it promotes coalescence particularly well because of its surface properties.

A discharge is preferably taken from the continuous organic phase in the upper region of the disengagement zone.

The discharge from the disengagement zone can, in a useful embodiment, be subjected to a work-up in order to isolate a fraction enriched in the aldol condensation product.

The discharge from the disengagement zone is preferably subject to a reaction in at least one further reactor. This enables the conversion into aldol condensation product(s) to be increased further. In particular, the further reaction is carried out in only one further reactor.

The further reaction is preferably carried out using at least one reactor having plug flow characteristics, i.e. a reactor which has very little backmixing in the flow direction. In a preferred variant, this reactor is tubular. To avoid backmixing and provide a relatively large surface area for the reaction, the reactor preferably comprises internals, i.e. ordered packing, e.g. sheet metal or woven packing, and/or a disordered bed of packing elements. Packings and packing elements are preferably composed of steel. The reactor having plug flow characteristics can be configured as a separate apparatus. In a specific embodiment, the reactor having plug flow characteristics is arranged directly above the first reactor which is operated in a backmixed manner.

The reactor used for the further reaction is preferably operated adiabatically. In a preferred embodiment, the reactor used for the further reaction comprises ordered packing, e.g. sheet metal or mesh packings, and/or a disordered bed of packing elements. Packings and packing elements are preferably composed of steel.

For the purposes of the present invention, the term "adiabatic" is used in the engineering sense rather than in the physicochemical sense. Adiabatic reaction conditions refer to a mode of operation in which the heat liberated in the reaction is taken up by the reaction mixture in the reactor and no cooling by means of cooling devices is employed. The heat of reaction is therefore discharged with the reaction mixture from the reactor, apart from a residual proportion which is given off from the reactor to the surroundings by natural heat conduction and thermal radiation.

A high final conversion in the reaction discharge can be achieved by means of the process of the invention. The reaction discharge is the discharge from the disengagement zone or, if present, the last reactor in the flow direction used for the aldol condensation. The conversion obtained by the process of the invention is preferably at least 95% by weight, preferably at least 97% by weight, based on the total weight of the linear aldehyde used for aldol condensation.

After the product mixture has been discharged from the disengagement zone or the after-reactor, it can be subjected to cooling, e.g. in a downstream heat exchanger.

The liquid reaction discharge is preferably separated into catalyst phase and product phase in a liquid-liquid separation vessel. This can be carried out in settling vessels of various construction types or centrifuges.

The water of reaction formed in the aldol condensation dilutes the catalyst solution and therefore has to be continually removed from the process. In the process of the invention, the removal of water preferably occurs exclusively with the liquid discharge from the disengagement zone or, if present, the (last in the flow direction) after-reactor. The aqueous catalyst phase obtained after liquid-liquid separation can be discharged as wastewater from the process. In an alternative embodiment, the aqueous catalyst phase which has been separated off can, optionally after discharge of a small proportion and corresponding replacement by fresh catalyst solution, also be recirculated to the aldol condensation.

The product obtained after the catalyst phase has been separated off can be purified by known methods, e.g. by distillation.

The aldol condensation products prepared by the process of the invention can advantageously be used for preparing saturated alcohols by hydrogenation. The saturated alcohols obtained in this way are employed, for example, for preparing plasticizers, detergents or solvents. The unsaturated $C_8$- and $C_{10}$-aldehydes are especially useful as precursors for plasticizer alcohols. Furthermore, the aldol condensation products can be converted by selective hydrogenation into the saturated aldehydes and these can be converted by subsequent oxidation into carboxylic acids, i.e. be used for the preparation of carboxylic acids. In addition, unsaturated aldehydes are used in many syntheses because of their reactivity. A further field of use of saturated and unsaturated aldehydes is use as fragrance.

DESCRIPTION OF FIGURES

The invention is illustrated below with the aid of FIGS. 1 and 2.

LIST OF REFERENCE NUMERALS (1) feed line for aldehyde
(2) two-fluid nozzle
(3) backmixed reaction zone
(4) circulation stream
(5) circulation pump
(6) external heat exchanger
(7) feed line for catalyst solution
(8) impingement plate
(9) disengagement zone
(10) reactor discharge
(11) after-reactor One possible embodiment of the invention is shown for the purposes of illustration in FIG. 1. The aldehyde feed (1) goes via a two-fluid nozzle (2) into the backmixed reaction zone (3) of the reactor. Mixing of the reaction zone and dispersion of the organic phase are effected by the introduced momentum of the driving jet of the nozzle. The circulation stream (4) which has been taken off in the lower region of the reactor and has previously been compressed by means of a circulation pump (5) and conveyed through an external heat exchanger (6) to remove the heat of reaction serves as driving jet. The concentrated catalyst solution (7) is introduced into the circulation stream. An impingement plate (8) can be provided at the bottom of the reactor in order to aid precipitation of organic droplets. The reaction zone is predominantly filled with aqueous phase in which the dissolved catalyst is present. Organic droplets comprising the reaction starting materials and reaction products are dispersed therein. Coalescence of the organic droplets and settling of the aqueous phase occur in the disengagement zone (9). This can be filled with ordered packing or with random packing elements which promote coalescence. In addition, residual conversion takes place here, i.e. the disengagement zone also serves as after-reactor. In particular, branched aldehyde isomers which react more slowly are reacted here. Within the disengagement zone or at the outlet of the reactor, phase inversion takes place, i.e. a continuous organic phase in which aqueous droplets are dispersed is formed. The reactor output (10) is taken off at the top of the reactor. It comprises predominantly organic phase. The aqueous phase comprises the dissolved catalyst and also water of reaction and water which was introduced via the catalyst stream.

Figure 1:
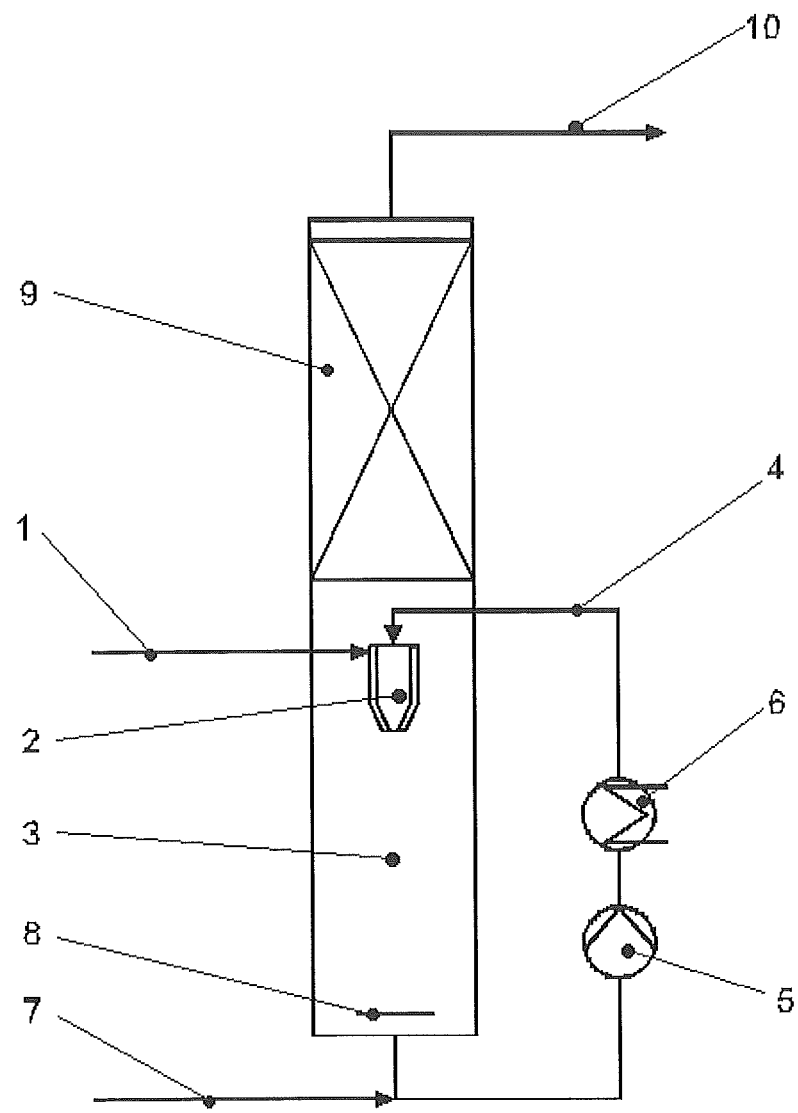
Figure 2:
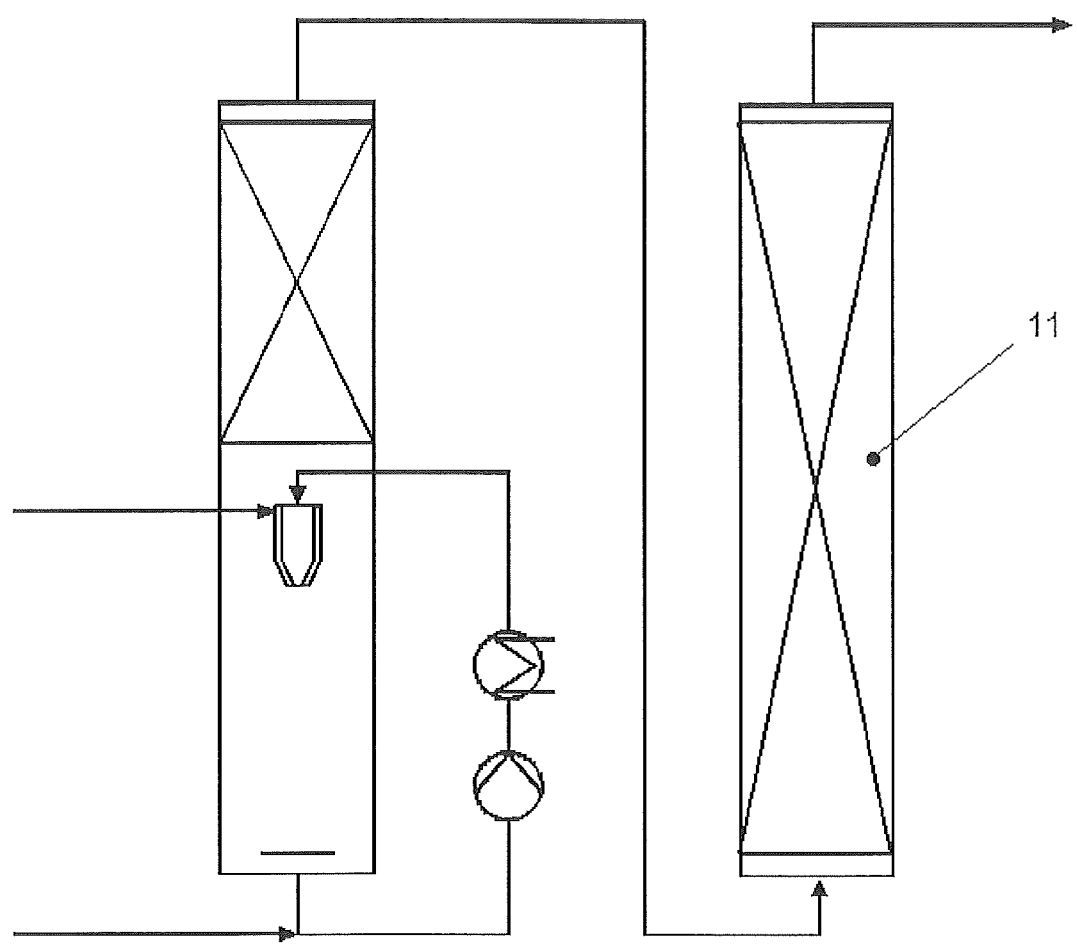

A further possible embodiment of the invention is shown in FIG. 2. There, an after-reactor (11) is installed downstream of the product outlet from the disengagement zone in order to achieve a higher conversion. The after-reactor can like the disengagement zone ((9) in FIG. 1) of the main reactor be provided with ordered packing or random packing elements in order to minimize axial backmixing, which leads to a higher reaction conversion and promotes coalescence of the two phases.

Example 1

An apparatus analogous to FIG. 2 was used. The first reactor had a height of 5.6 m and a diameter of 0.8 m in the lower part. This lower part was superposed by a second part having a height of 2.0 m and a diameter of 1.1 m. The lower part was mixed by means of a nozzle. In the upper part, 1 m³ of packing elements (Pall rings composed of V2A steel (1.4541) and having a diameter of 35 mm) were installed. The second reactor had a height of 16.3 m and a diameter of 0.5 m and was filled with 3.0 m³ of packing elements (Pall rings composed of V2A steel (1.4541) and having a diameter of 35 mm). The plant was supplied continuously with 8.4 t/h of an aldehyde mixture (88.8% of n-valeraldehyde; 9.8% of 2-methylbutanal; 0.2% of 3-methylbutanal, balance dissolved butanes and butenes). 20 t/h were conveyed through the pumped circuit. The two-fluid nozzle had an internal diameter of 26.7 mm and produced a pressure drop of 0.45 bar. The specific power input is 0.09 kW/m³. A superficial velocity of 3.2 mm/s is obtained in the packing in the first reactor. The sodium hydroxide concentration in the aqueous phase was maintained at 2.5% by weight by addition of 20% sodium hydroxide solution. A pressure of Pe=6 bar and a temperature of 145° C. were set in the two reactors.

The composition of the discharge was determined by GC analyses.

| Component | GC-% by area |
| --- | --- |
| n-Valeraldehyde | 1.4 |
| 2-Methybutanal | 4.9 |
| 3-Methylbutanal | 0.01 |
| 2-Propylheptenal | 81.2 |
| 4-Methyl-2-propylhexenal | 9.7 |
| 5-Methyl-2-propylhexenal | 0.4 |
| High boilers | 1.5 |

The conversions of the individual components were determined:

| Component | Conversion |
| --- | --- |
| n-Valeraldehyde | 98.6% |
| 2-Methybutanal | 55% |
| 3-Methylbutanal | 95% |

Example 2

An apparatus analogous to FIG. 1 was used. The reactor had a diameter of 1.5 m and a height of 14 m. The lower part was mixed by means of a nozzle. In the upper part, 8 m of structured packing composed of stainless steel (304 L) was installed. The plant was supplied continuously with 25 t/h of an aldehyde mixture (99.85% of n-butyraldehyde; 0.07% of isobutyraldehyde, balance is dissolved propane and propene). 135 t/h were conveyed through the pumped circuit. The two-fluid nozzle had an internal diameter of 50 mm and produced a pressure drop of 2.2 bar. The specific power input is 0.75 kW/m³. A superficial velocity of 6 mm/s is obtained in the packing in the reactor. The sodium hydroxide concentration in the aqueous phase was maintained at 4.0% by weight by addition of 25% sodium hydroxide solution. A pressure of Pe=2.75 bar and a temperature of 90° C. were set in the reactor.

The composition of the discharge was determined by GC analyses.

| Component | GC-% by area |
| --- | --- |
| n-Butyraldehyde | 0.4 |
| Isobutyraldehyde | 0.01 |
| 2-Ethylhexenal | 96.9 |
| 4-Methyl-2-ethylpentenal | 0.15 |
| High boilers | 2.2 |

The conversions of the individual components were determined and found to be as follows:

| Component | Conversion |
| --- | --- |
| n-Butyraldehyde | 96.4% |
| Isobutyraldehyde | 86% |

The invention claimed is:
1. A process for the catalytic aldol condensation of at least one aldehyde in a two-phase liquid reaction mixture in a reactor which has a reaction zone and a disengagement zone located directly above the reaction zone, wherein the reaction zone is backmixed, and wherein an aldehyde-comprising phase dispersed in a continuous aqueous catalyst-comprising phase is produced and a stream of the two-phase reaction mixture is allowed to rise from the reaction zone into the disengagement zone and coalesce, with a continuous organic phase being formed in the upper region of the disengagement zone.

2. The process according to claim 1, wherein the reaction zone and the disengagement zone are located in a single reaction vessel.

3. The process according to claim 1, wherein the proportion by volume of the aqueous phase in the reaction zone is at least 70%, or at least 80%, based on the total volume of the two-phase reaction mixture in the reaction zone.

4. The process according to claim 1, wherein at least one stream fed into the reaction zone and/or at least one stream from the reaction zone conveyed in an external circuit (circulation stream) is/are used for backmixing.

5. The process according to claim 1, wherein the reaction zone is configured as a loop reactor or stirred vessel.

6. The process according to claim 1, wherein the reaction zone is configured as a free jet reactor.

7. The process according to claim 1, wherein the aldehyde is introduced in the upper region of the reaction zone.

8. The process according to claim 1, wherein at least one mixing nozzle is used to produce the aldehyde-comprising phase dispersed in the continuous aqueous catalyst-comprising phase in the reaction zone.

9. The process according to claim 8, wherein the total mixing power introduced into the reactor is not more than 0.5 kW per $m^3$ of liquid volume, or not more than 0.3 kW per $m^3$ of liquid volume.

10. The process according to claim 1, wherein the aldehyde is introduced via a two-fluid nozzle.

11. The process according to claim 10, wherein the aldehyde and a stream from the reaction zone conveyed in an external circuit (circulation stream) are introduced into the two-fluid nozzle.

12. The process according to claim 1, wherein the disengagement zone and the reaction zone are tubular and the disengagement zone has a greater diameter than the reaction zone.

13. The process according to claim 1, wherein the disengagement zone comprises internals and/or packing elements arranged therein.

14. The process according to claim 1, wherein a discharge is taken off from the continuous organic phase in the upper region of the disengagement zone.

15. The process according to claim 14, wherein the discharge from the disengagement zone is subjected to a further reaction in at least one reactor.

16. The process according to claim 15, wherein at least one adiabatically operated reactor is used for the further reaction.

17. The process according to claim 16, wherein the reactor used for the further reaction comprises internals and/or packing elements.

* * * * *